US00PP30639P2

(12) United States Plant Patent
Stanley

(10) Patent No.: US PP30,639 P2
(45) Date of Patent: Jul. 2, 2019

(54) HEMP PLANT NAMED 'CW2A'

(50) Latin Name: ***Cannabis sativa* L.**
Varietal Denomination: CW2A

(71) Applicant: CWB Holdings, Inc., Denver, CO (US)

(72) Inventor: Joel Stanley, Larkspur, CO (US)

(73) Assignee: CWB Holdings, Inc., Denver, CO (US)

( * ) Notice: Subject to any disclaimer, the term of this patent is extended or adjusted under 35 U.S.C. 154(b) by 0 days.

(21) Appl. No.: 15/932,859

(22) Filed: May 10, 2018

(51) Int. Cl.
*A01H 5/00* (2018.01)

(52) U.S. Cl.
USPC ..... Plt./258

(58) Field of Classification Search
USPC ..... Plt./263.1, 258
CPC ..... A01H 5/12; A01H 5/00; A01H 6/28
See application file for complete search history.

(56) References Cited

U.S. PATENT DOCUMENTS

PP27,475 P2 * 12/2016 Kubby ..... A01H 5/00
Plt./263.1

OTHER PUBLICATIONS

Ingold. Desperate Journey: CBD in Colorado Story 4 Pushing Ahead, The Denver Post Dec. 9, 2014, pp. 1-8. (Year: 2014).*
Kentucky Department of Agriculture Industrial Hemp Research Pilot Program Summary of Varieties: Including Varieties of Concern and Prohibited Varieties, retrieved on Jul. 11, 2018, retrieved from the Internet at http://www.kyagr.com/marketing/documents/HEMP_LH_Summary-of-Varieties.pdf, pp. 1-4, 2018. (Year: 2018).*
Leinow L. & Birnbaum J., foreword by Michael H. Moskowitz, MD., "CBD: A Patient's Guide to Medicinal Cannabis," sponsored by published by the Society for the Study of Native Arts and Sciences (dba North Atlantic Books) Chapter 8, (2017), 23 pages.

* cited by examiner

*Primary Examiner* — June Hwu
(74) *Attorney, Agent, or Firm* — Cooley LLP

(57) ABSTRACT

The present invention provides a new and distinct hemp cultivar designated as 'CW2A'.

13 Drawing Sheets

Latin name of genus and species: *Cannabis sativa* L.
Variety denomination: 'CW2A'.

BACKGROUND OF THE INVENTION

*Cannabis* is a genus of flowering plants that includes at least three species, *Cannabis sativa, Cannabis indica,* and *Cannabis ruderalis* as determined by plant phenotypes and secondary metabolite profiles. In practice however, *Cannabis* nomenclature is often used incorrectly or interchangeably.

Hemp, also known as industrial hemp, is a type of *Cannabis* plant grown specifically for the industrial uses of its derived products. Hemp by definition has no more than three-tenths of one percent (i.e., 0.3%) concentration of tetrahydrocannabinol (THC). THC causes psychoactive effects when consumed and is typically associated with marijuana (i.e., *Cannabis* with higher THC contents). Hemp extracts produced from industrial hemp, such as extracts produced from 'CW2A', have no such psychoactive effects due to their low THC content. Values of total CBD and total THC obtained from laboratory testing of dried mature female flowers may show variance that results from differing growing environments, sampling methodologies, and testing techniques.

The present invention relates to a new and distinct hemp (*Cannabis sativa* L.) cultivar designated as 'CW2A'. Whole-plant hemp extracts from 'CW2A' contain an assortment of phytocannabinoids (e.g., CBD), terpenes, flavonoids and other minor but valuable hemp compounds that work synergistically to heighten effects of products produced from 'CW2A'. This synergistic effect is sometimes referred to as the "entourage effect". 'CW2A' extracts can be used to produce a variety of products, including liquid and capsule forms for oral administration, topical products, cosmetic products, infused beverages, sport products and hemp-infused pet treats.

Despite *Cannabis* being consumed since at least the third millennium BC, complete scientific corroboration for uses of CBD are still in their infancy. Industry reports suggest CBD is used for a variety of health and wellness purposes, including as a sleep aid, coping with daily stress, fighting anxiety, relieving pain, assisting with cognitive function and boosting immune health. Significant research is currently being conducted at a variety of laboratories on the use of CBD as it relates to epilepsy, Post-Traumatic Stress Disorder (PTSD), cancer, autism, neuroprotection, anti-inflammatory effects, anti-tumor effects and anti-psychotic effects.

'CW2A' is a selection resulting from controlled-crosses using hemp germplasm from different regions of the United States. The primary goal of the breeding program was to develop a new hemp variety with high cannabidiolic acid (CBDA) concentrations and low tetrahydrocannabinolic acid (THCA) concentrations in its mature female flowers. Of the females tracing back to the original cross, the healthiest and most vigorous individual that showed no monoecious tendencies without stress manipulation was chosen to be 'CW2A'.

The new cultivar of 'CW2A' was asexually reproduced via stem cuttings from vegetative and/or flowering plants, and cloning by the inventor at the inventor's greenhouses, nurseries, fields and/or facilities in Colorado Springs, Colo. and Wray, Colo. Asexual clones from the original source have been tested in greenhouses, nurseries, and/or fields. The properties of each clone from this cultivar were found to be transmissible by such asexual reproduction. The cultivar is stable and reproduces true to type in successive generations of asexual reproduction (i.e., clones from 'CW2A' are uniform).

BRIEF SUMMARY OF THE INVENTION

This invention relates to a new and distinctive hemp cultivar designated as 'CW2A'.

As used herein, the term "cultivar" is used interchangeably with "variety", "strain", and/or "clone".

The inventor reproduced progenies asexually by stem cutting from vegetative and/or flowering plants, and cloning. The plant has been and continues to be asexually reproduced by stem cutting from vegetative and/or flowering plants, and cloning at the inventor's greenhouses, nurseries, fields and/or facilities in Colorado Springs, Colo. and Wray, Colo.

DESCRIPTION OF THE DRAWINGS

The accompanying color photographs depict characteristics of the new 'CW2A' plants as nearly true as possible to make color reproductions. The overall appearance of the 'CW2A' plants in the photographs is shown in colors that may differ slightly from the color values described in the detailed botanical description.

DETAILED BOTANICAL DESCRIPTION

Figure 1:
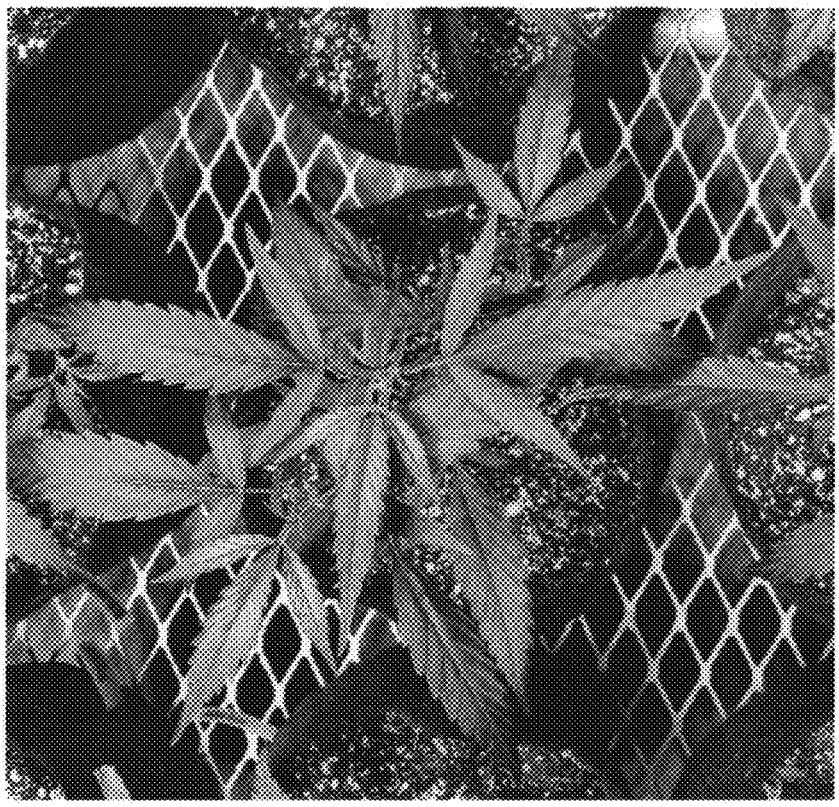
FIG. 1 shows an overall view of the 'CW2A' indoor plant at the early to mid vegetative growth stage with lateral branches and further intermodal growth as shown from above.
Figure 2:
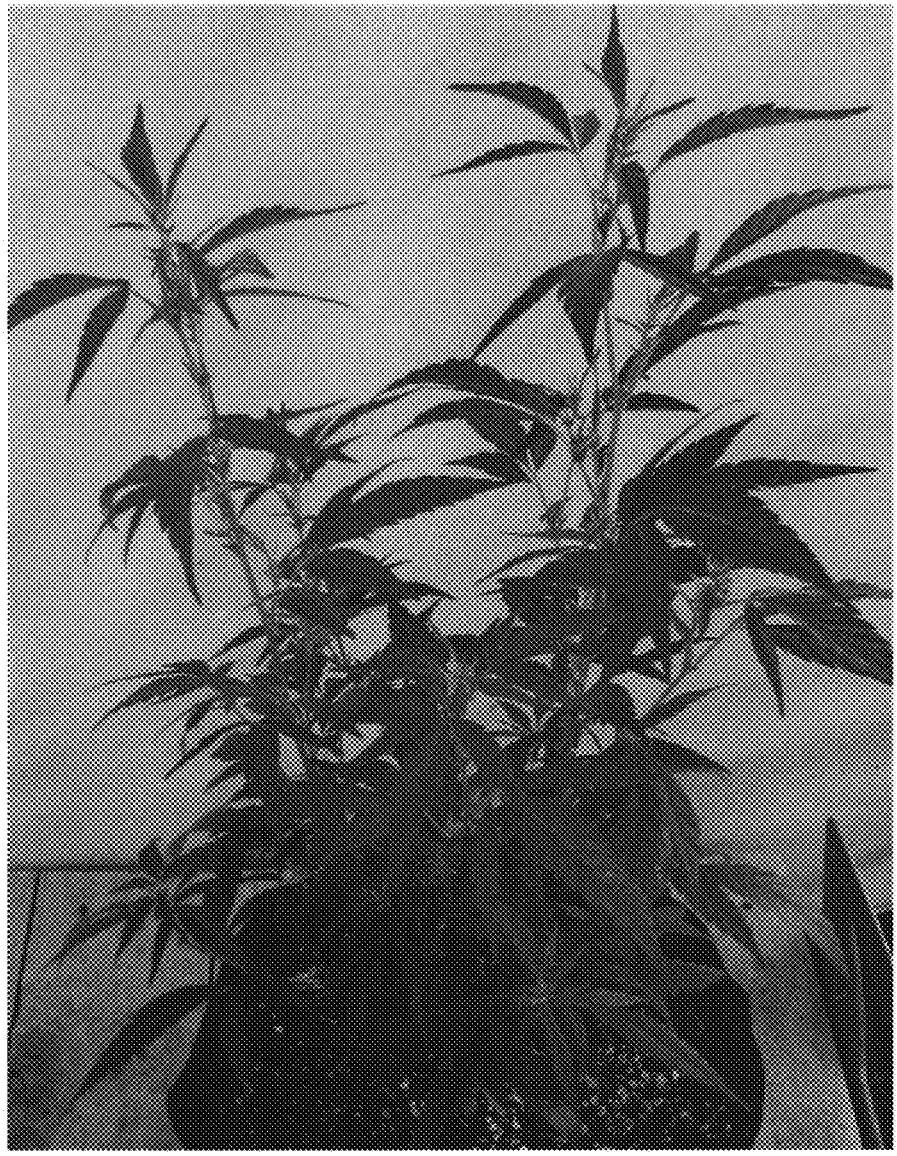
FIG. 2 shows an overall view of the 'CW2A' indoor plant during the mid to late vegetative growth stage as shown from the side.
Figure 3:
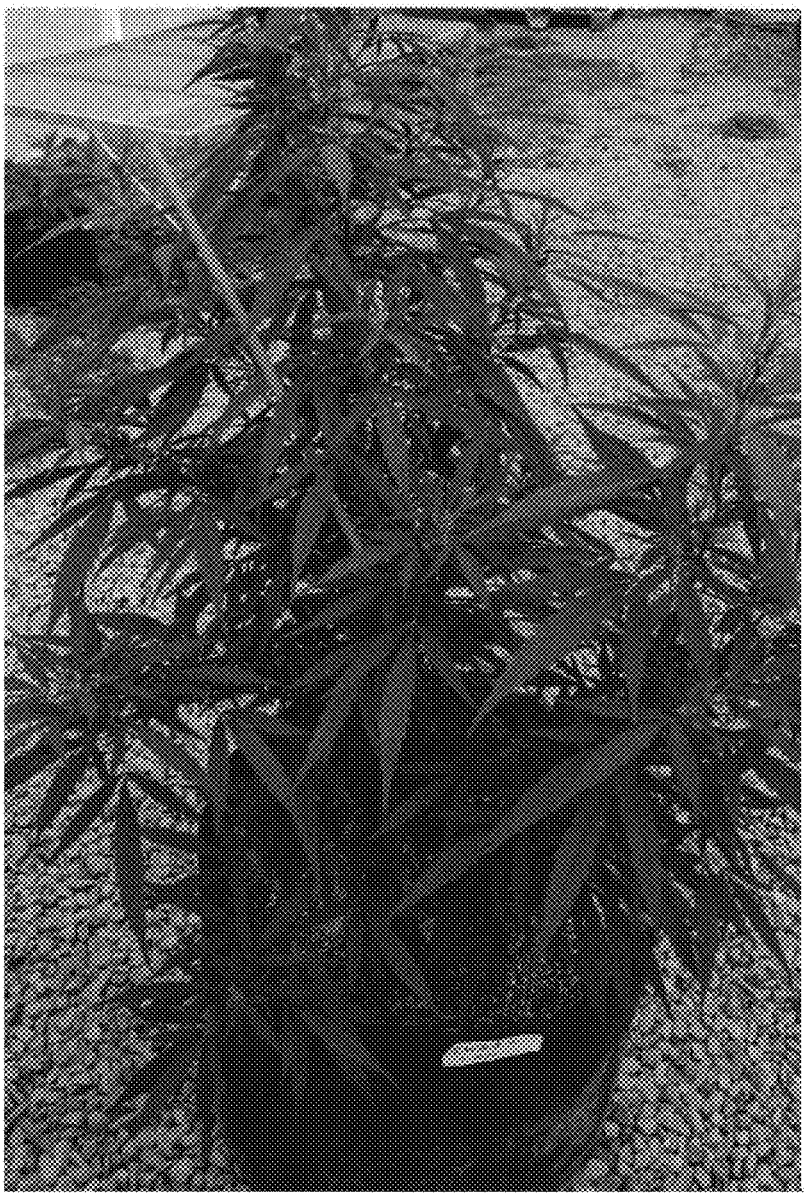
FIG. 3 shows an overall view of the 'CW2A' indoor plant during the mid to late vegetative growth stage as shown from the side.
Figure 4:
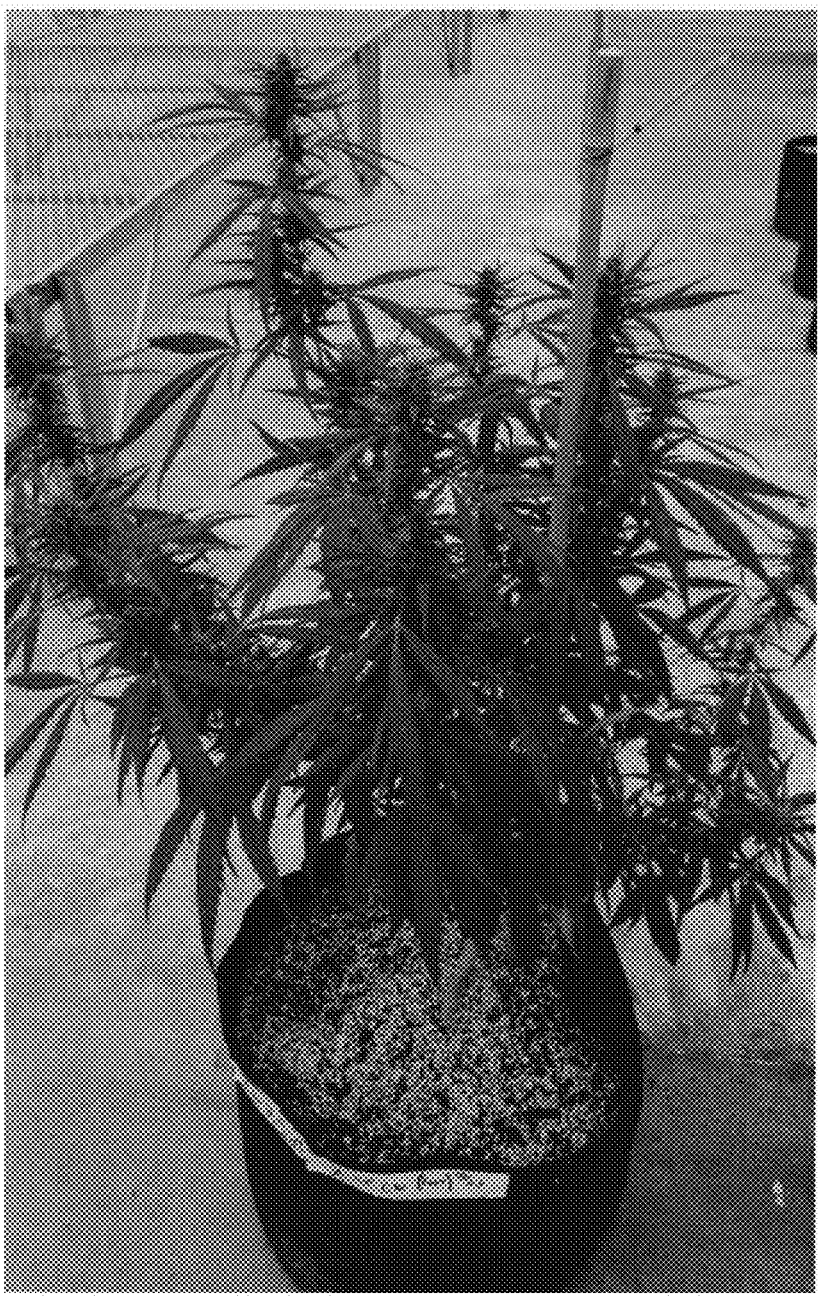
FIG. 4 shows an overall view of the 'CW2A' indoor plant at the early to mid flowering stage as shown from the side.
Figure 5:
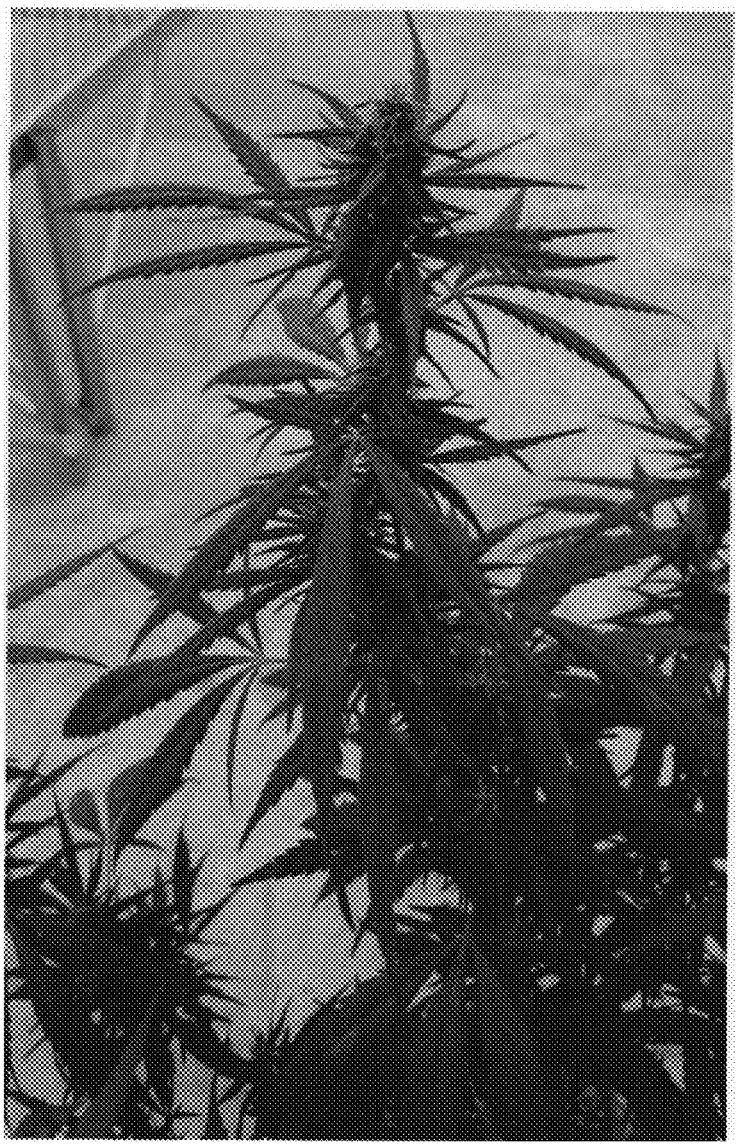
FIG. 5 shows a close view of flowers of the 'CW2A' indoor plant at the early to mid flowering stage.
Figure 6:
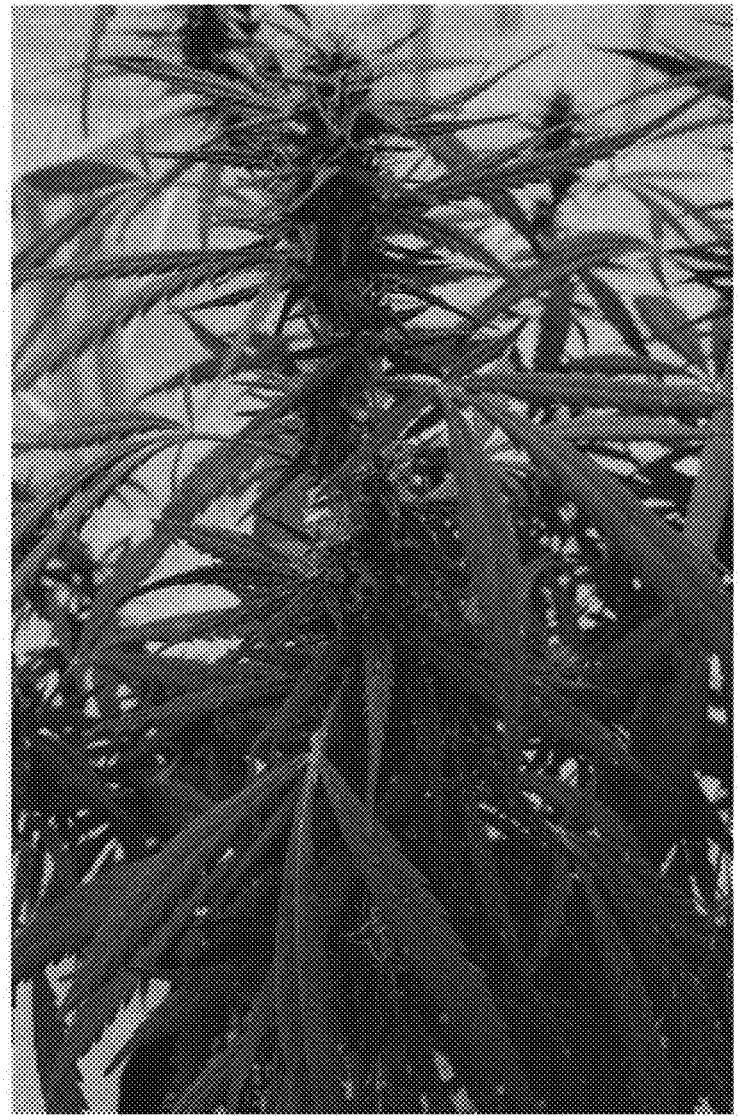
FIG. 6 shows another close view of flowers of the 'CW2A' indoor plant at the early to mid flowering stage.
Figure 7:
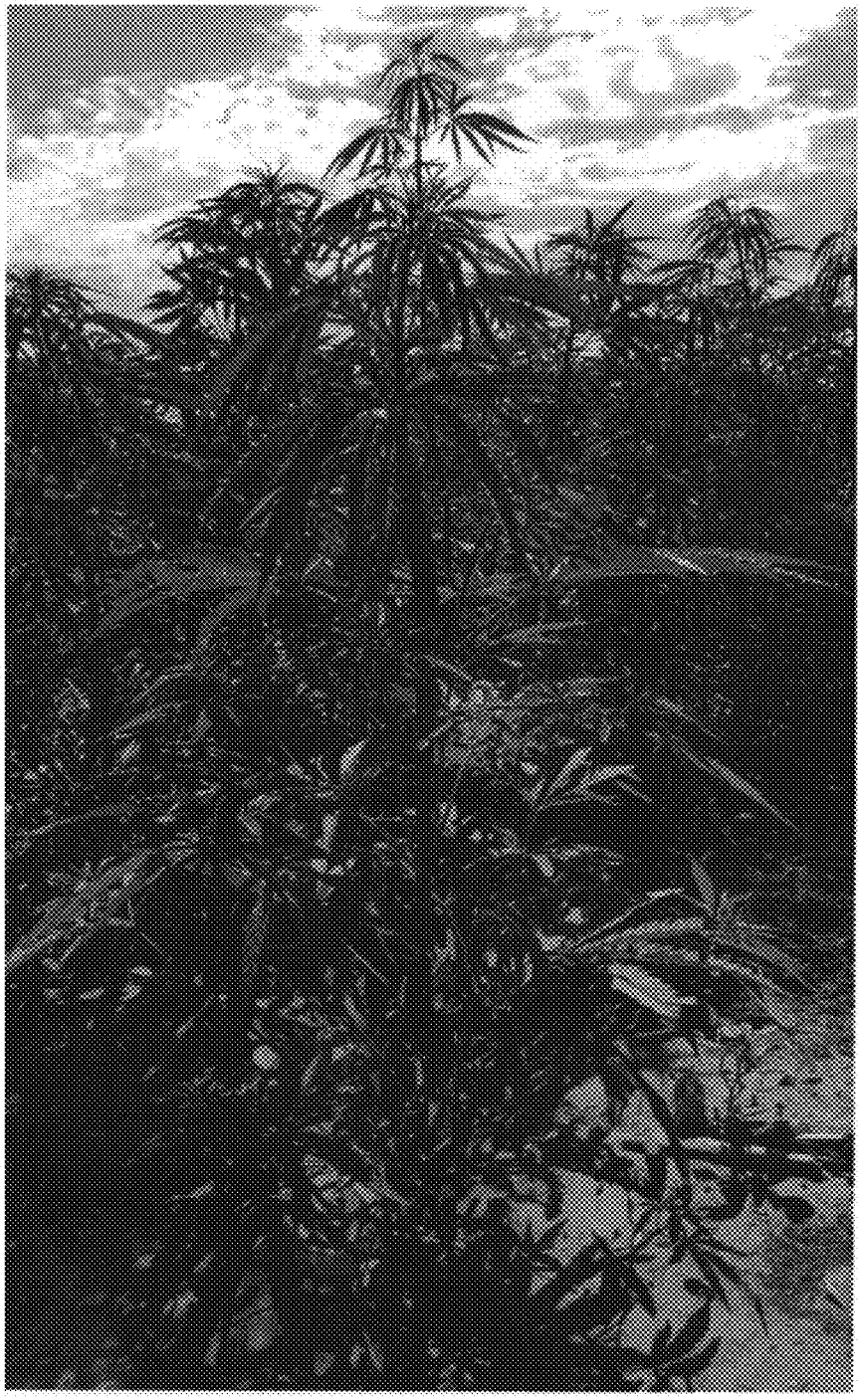
FIG. 7 shows an overall view of the 'CW2A' outdoor plant at the mid vegetative growth stage as grown in the field.
Figure 8:
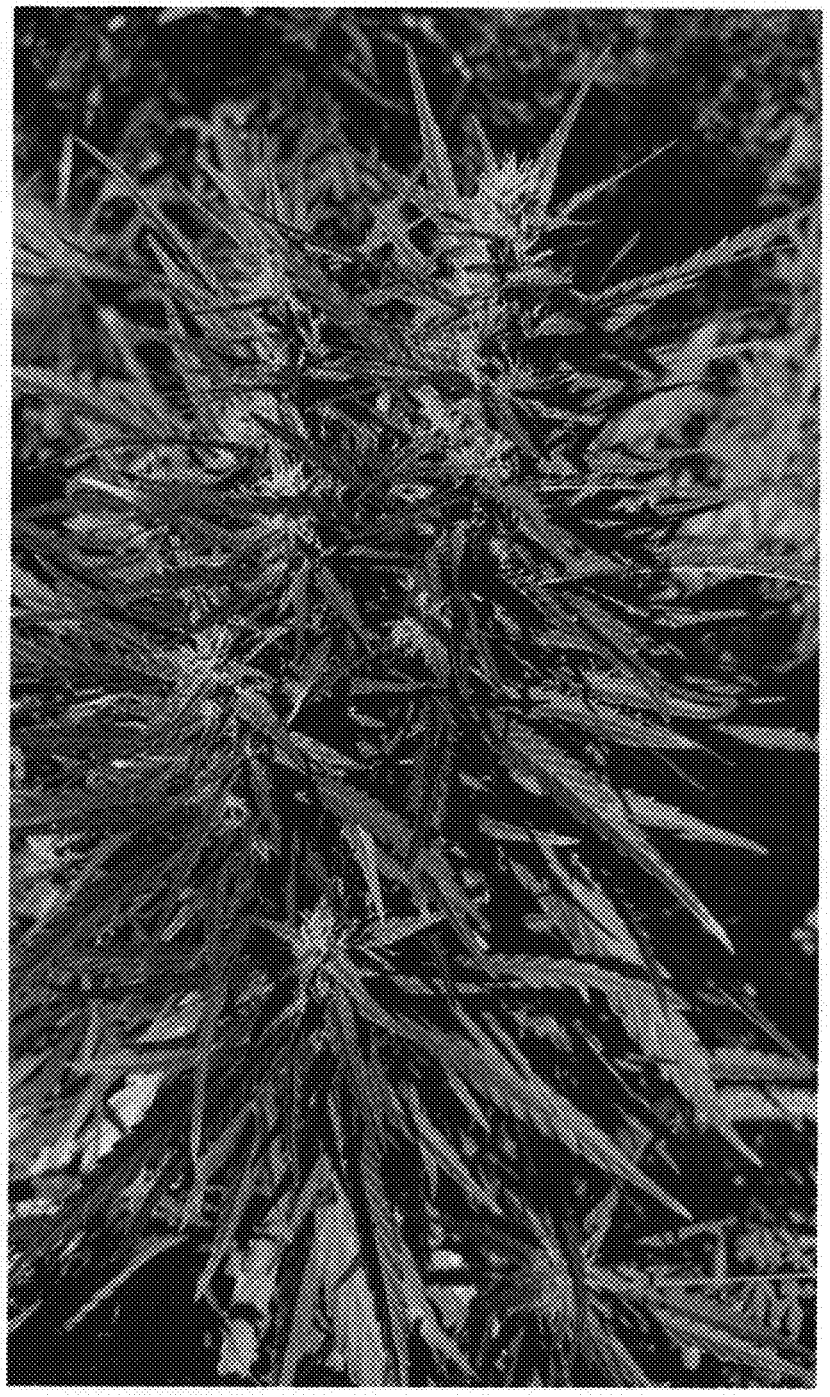
FIG. 8 shows a close view of flowers of the 'CW2A' outdoor plant at the early to mid flowering stage as grown in the field.
Figure 9:
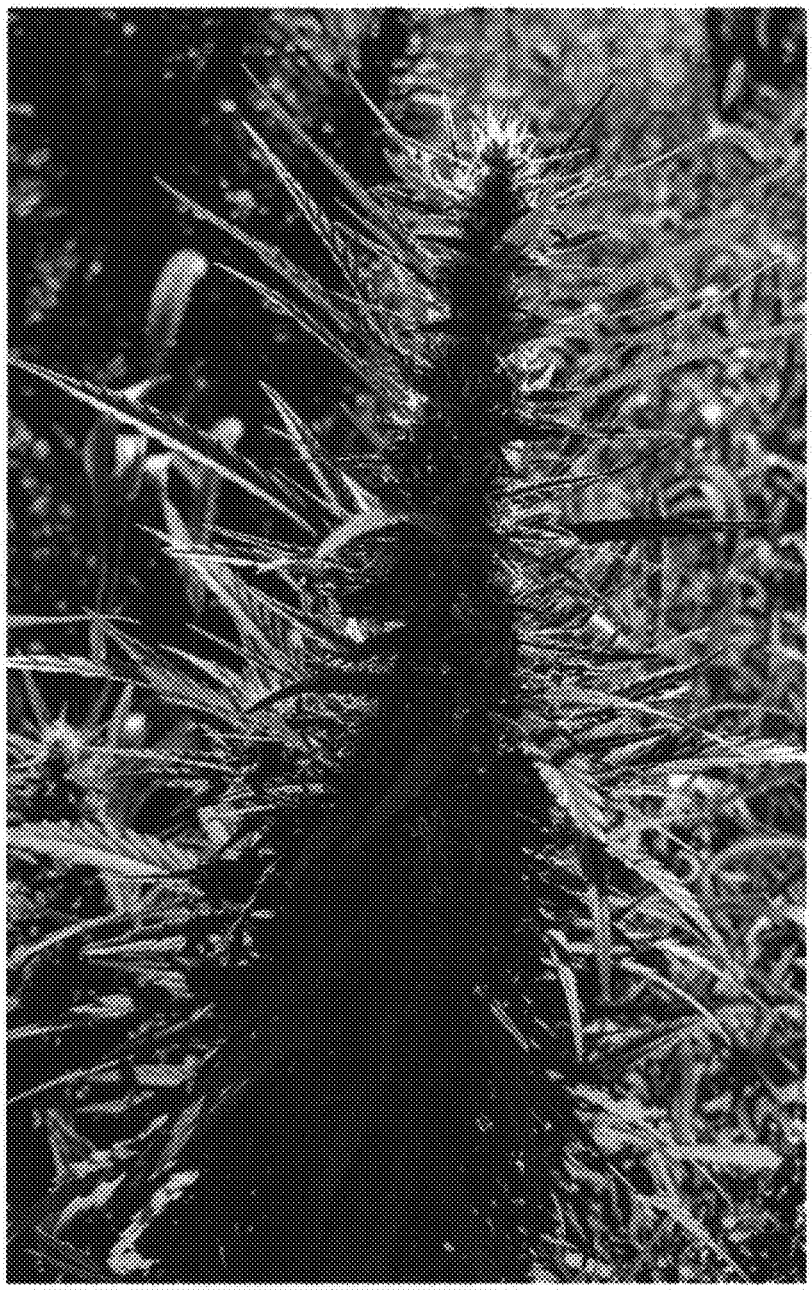
FIG. 9 shows an overall view of upper part (including flowers) of the 'CW2A' outdoor plant at the early to mid flowering stage as grown in the field.

'CW2A' has not been observed under all possible environmental conditions, and the phenotype may vary significantly with variations in environment. The following observations, measurements, and comparisons describe this plant as grown at Wray, Colo., when grown in the greenhouse, nursery or field, unless otherwise noted.

Plants for the botanical measurements in the present application are annual plants. In the following description, the color determination is in accordance with The Royal Horticultural Society Colour Chart, Sixth Edition (2015), except where general color terms of ordinary dictionary significance are used.

'CW2A' is a fertile hybrid derived from a controlled-cross between proprietary cultivar '1AC' as the female parent (i.e., pollen accepter) and another hemp plant as the male parent (i.e., pollen donor) originating from a feral hemp (a.k.a. ditch weed) population in Colorado with an unknown cannabinoid content ("Feral Male Parent").

Breeding History of the Female Parent. The lineage of proprietary female parent '1AC' comprises four generational crossings. The first crossing was made between a parental female from a cutting of *Cannabis sativa* L. originating in Colorado of unknown parentage ("First Female $F_0$") with a parental male plant ("First Male $F_0$") which originated from a feral hemp population in Colorado with an unknown cannabinoid content. Of the resulting progeny, 40 seeds were germinated and developed into 24 female ("$F_1$ Females") and 16 male ("$F_1$ Males") plants.

For the second crossing, an egg donor from a female clone of *Cannabis sativa* L. with unknown genealogy ("Second Female") was crossed to a healthy vigorous $F_1$ Male from the first cross. Of the resulting offspring, twenty seeds were germinated of which 70% were female ("$F_2$ Females") and 30% were male ("$F_2$ Males").

For the third crossing, a single $F_2$ Female was chosen and crossed with a sibling of First Male $F_0$. Of the resulting progeny, fifty seeds were germinated. Twenty-five seedlings were female ("$F_3$ Females") and 25 were male ("$F_3$ Males").

The fourth generation was produced by crossing two $F_3$ Females that displayed the most vigor and health. Both $F_3$ Females chosen for the cross were short and squat in stature, had medium to broad leaf structure with tight internodes of about ½ inch, and displayed a 70-75 day flowering maturity after flowering initiated. The $F_3$ Female was chosen as the egg donor ("$F_3$-e") for the fourth generation. The $F_3$ female was also chosen as the pollen donor ("$F_3$-p") for the fourth generation. The $F_3$-p female was induced to produce male flowers, thus generating pollen, using heat and erratic photoperiod stress techniques. $F_3$-e was pollinated by $F_3$-p and generated progeny ($F_4$) that were all female with slightly different characteristics. All $F_4$ plants exhibited *indica*-dominant traits such as medium to broad leaf structure, short squat overall growth habit, and tight internodes with full flower maturity taking roughly 65-70 days after flowering initiated. About 90% of all $F_4$ plants exhibited resistance to pests and diseases and showed great health and vigor throughout the entire lifecycle. Few plants displayed white and/or yellow coloration similar to marbling on the leaves.

Of these $F_4$ females, the healthiest and most vigorous individual was chosen to be '1AC'.

Breeding History of the Male Parent. The Feral Male Parent of 'CW2A' was the most vigorous and healthy male with broad, palmately compound leaves and squat stature at maturity ("*indica*-dominant") which germinated from a feral hemp population. Ten seeds of the resulting offspring were germinated. Of the ten seeds, six were male and four were female. Ninety percent of all individuals exhibited resistance to pests and diseases and showed great health and vigor throughout the entire lifecycle. Nearly all of the males grew taller than the females and exhibited medium to broad leaf structure similar to *indicia/sativa* hybrid characteristics. The Feral Male Parent is not a genetically modified organism.

Crossing of Parental Lines. '1AC' was crossed to the Feral Male Parent and all of the resulting females displayed long and slender leaflets, leaves, and overall growth pattern ("*sativa*-dominant"). Of the females, 75% exhibited monecious characteristics without stress manipulation. All females showed premature flowering without a change in light duration; although change in light duration to 12 hours of light and 12 hours of dark within a 24-hour period induced all females into a distinct flowering cycle. Of these females, the healthiest and most vigorous individual, that showed no monecious tendencies without stress manipulation was chosen to be 'CW2A'.

TABLE I

| General | |
|---|---|
| Characteristics | New Variety |
| Plant life forms | An herbaceous plant (herb) |
| Plant growth habit | An upright, dioecious annual plant with hermaphroditic tendencies, and at maturity 1-4 meters in height depending on growth conditions Having no hermaphroditic (monecious) tendencies without stress manipulation |
| Plant origin | Female progeny of a cross between '1AC' Female Parent and Feral Male Parent |
| Plant propagation | Asexually propagated by cutting and cloning such as vegetative stem cuttings as well as stem cuttings from flowering plants |
| Propagation ease | Easy |
| Propagation condition | Adventitious root structures readily form from stem tissue when submerged in rooting media, including soil, rockwool, aeroponics, etc., when adequate amounts of oxygen and moisture are supplied, and ambient temperatures are between 55-75 degrees Fahrenheit with appropriate lighting conditions. |
| Height (Unit: meter and/or feet) | 1-4 m at maturity Height and shape depends on planting pattern such as planting date and density. With about 2 feet or less close spacing between plants, plants can be up to 10 feet tall at maturity with thinner pseudospike flower characteristics. Generally, plant height is twice as much as plant width. |
| Width (Unit: meter) | 0.4-2 m |
| Plant vigor | High The most vigorous growth in late vegetative stage before flowering stage. |
| Time to Harvest | 100-135 days |
| Resistance to pests or diseases | Resistant to common viruses and fungal diseases Susceptible to molds and mildews if grown indoors without proper ventilation and constantly maintaining greater than 60% relative humidity Susceptible to *Phytophothora* spp., Fusarium spp., and *Pythium* spp. |
| Genetically-modified organism | No |

TABLE I-continued

| General | |
|---|---|
| Characteristics | Parental variety ('MC') (Female plant) |
| Plant life forms | An herbaceous plant (herb) |
| Plant growth habit | An upright, shrub-like dioecious annual plant with a rigid branching herbaceous stalk, reaching 0.5-3 meters in height and 0.5-3 meters in width in one growing season |
| Plant origin | '1 AC' *Cannabis sativa* L. |
| Plant propagation | Asexually propagated by cutting and cloning such as vegetative stem cuttings as well as stem |
| Propagation ease | Easy |
| Propagation condition | Adventitious root structures readily form from stem tissue when submerged in rooting media, including soil, rockwool, aeroponics, etc., when adequate amounts of oxygen and moisture are supplied, and ambient temperatures are between 55-75 degrees Fahrenheit with appropriate lighting conditions. |
| Height (Unit: meter and/or feet) | 0.5-3 m at maturity Stalky and bushy with round footprint. With adequate spacing, plant height is approximately equal to width. |
| Width (Unit: meter) | 0.5-3 m |
| Plant vigor | High The most vigorous growth in late vegetative stage before flowering stage. |
| Time to Harvest | 120-140 days |
| Resistance to pests or diseases | Resistant to most viruses and fungal diseases common to grain and vegetable crops Slightly susceptible to powdery mildew and *Botrytis* spp. if grown in greenhouses, or indoors, without proper ventilation and consistently maintaining greater than 65% relative humidity. Slightly less susceptible to *Phytophothora* spp., *Fusarium* spp., and *Pythium* spp. except for in greenhouse. |
| Genetically-modified organism | No |

TABLE II

| Leaf/Foliage | |
|---|---|
| Characteristics | New Variety |
| Leaf arrangement | Opposite in early vegetative growth stages especially on main axis if grown from seed A tendency toward alternate arrangements on axillary branches once the flowering stage begins or when taken as a vegetative cutting typically observed Phyllotaxy depends on growth conditions and on whether individuals are derived from vegetative or seed propagation |
| Leaf shape | Palmately compound |
| Leaf structure | Serrated margins, lightly acicular to lanceolate leaflets, tapering to an acuminate apex |

TABLE II-continued

| Leaf/Foliage | |
|---|---|
| Leaf margins | Jaggedly serrate with each tooth apex angled toward leaflet apex Apical side of tooth is concave and basal side of tooth is convex |
| Leaf hairs | Absent |
| Leaf length with petiole at maturity (Unit: cm or inches) | 12-24 cm |
| Petiole length at maturity (Unit: cm) | 4.2-8.0 cm |
| Petiole color (RHS No.) | Very slightly lighter (whiter) than RHS 144A |
| Anthocyanin color and intensity in Petioles | RHS 59A to 187A and 187B when present Anthocyanin coloration ranges from total absence to minute but pronounced mixture with normal green coloration on adaxial surface of petiole during vegetative growth stage During flowering stage, anthocyanin pigmentation on petioles of so called fan leaves intensifies and covers both adaxial and abaxial surfaces; Darker adaxial surfaces are still RHS 59A to 187A; Abaxial surfaces are lighter and less densely colored with a range of coloration RHS 184A; to 180A; to 178A through 178B; to 176A |
| Stipule length at maturity (Unit: cm) | 0.4-0.9 cm |
| Stipule shape | Up to 1.0 cm, spinose with a wider base about 1.0 mm or more thick tapering to spinose tip Light green center with white green edges and a folded, v-shape in cross section Sometimes curvaceous growth |
| Stipule color (RHS No.) | Green portions of stipule vary from RHS 143A to the light yellow white of the edges RHS 4D |
| No. of leaflets | 3-5 in immature plants, as many as 9 at maturity |
| Middle largest (longest) leaflet length (Unit: cm) | 7-15.9 cm |
| Middle largest (longest) leaflet width (Unit: cm) | 1.5-2.0 cm |
| Middle largest (longest) leaflet length/width ratio | About 4:1-8:1 |
| No. teeth of middle leaflet | 19-29 |
| Leaf (upper side-adaxial) color (RHS No.) | RHS 137A before flowering stage Very close to (a little darker/bluer) RHS NN137A during flowering stage Yellow in late flowering stage |
| Leaf (lower side-abaxial) color (RES No.) | Between RHS 146D and RHS 147C before flowing stage Between RHS NN137D and RHS 147B during flowering stage |
| Leaf glossiness | Very slight sheen, but not glossy |
| Vein/midrib shape | Midvein is straight down the middle of each leaflet. Secondary veins are percurrent, branched alternately from midvein, and grow to tooth apex |
| Vein/midrib color (RHS No.) | RHS 143C |
| Aroma | An earthy aromatic herbal smell with a hint of citrus/pine scent and a general sweetness |

TABLE II-continued

| Leaf/Foliage | |
|---|---|
| Characteristics | Parental variety (1AC) (Female plant) |
| Leaf arrangement | Alternate with short internodes during early vegetative growth stages especially after cloning Sometimes opposite (seedling vegetative stage) and whorled (flowering stage) leaf positioning depending on growth conditions and vegetative or seed propagation Phyllotaxy depends on growth conditions and on whether individuals are derived from vegetative or seed propagation |
| Leaf shape | Palmately compound |
| Leaf structure | Serrated, lanceolate, pinnately veined leaflets with a medium to dark green upper surface and light green to white green lower surface. Broader leaflets than CW2A |
| Leaf margins | Plane with tooth apices angled toward leaflet apex Jaggedly serrated when leaves are immature, developing into not so jaggedly serrated when leaves/leaflets are mature Both apical and basal side of tooth are generally convex |
| Leaf hairs | Absent |
| Leaf length with petiole at maturity (Unit: cm or inches) | Typically 3"-7" inches. Up to 10" inches in the field with optimal growing conditions and at peak vegetative growth |
| Petiole length at maturity (Unit: cm) | 5.1 cm-10.2 cm dependingon leaf type (on axillary branch node vs main axis, subtending inflorescence, immature/mature, etc.) |
| Petiole color (RHS No.) | Between RHS145A and 145B |
| Anthocyanin color and intensity in Petioles | N/A |
| Stipule length at maturity (Unit: cm) | <1 cm |
| Stipule shape | Linear with slight curvaceous growth. Sometimes slightly wider than those in CW2A and occasionally flower primordia containing a thin white filament hair similar to a mature stigma are found |
| Stipule color (RHS No.) | N/A |
| No. of leaflets | 3-7 in immature plants, 5-9 at maturity |
| Middle largest (longest) leaflet length (Unit: cm) | 6-15 cm |
| Middle largest (longest) leaflet width (Unit: cm) | 2.5-4.0 cm |
| Middle largest (longest) leaflet length/width ratio | About 4:1 |
| No. teeth of middle leaflet | 26-37 |
| Leaf (upper side-adaxial) color | RHS NN137B |
| Leaf (lower side-abaxial) color (RES No.) | RHS 147B |
| Leaf glossiness | Slightly glossy, especially at maturity |
| Vein/midrib shape | Midvein is straight down the middle of each leaflet. Secondary veins are percurrent, branched alternately from midvein, grow to tooth apex with |

TABLE II-continued

| Leaf/Foliage | |
|---|---|
| | some forming loops to other secondary veins, and more apparent tertiary venation, especially in mature leaflets |
| Vein/midrib color (RHS No.) | RHS 145C |
| Aroma | A pleasantly earthy aromatic, strong, peculiar smell with a hint of pine scent |

TABLE III

| Stem | |
|---|---|
| Characteristics | New Variety |
| Stem shape | Round at maturity<br>Very slightly squared in immature axillary branches and at immature growth stages<br>Finely pubescent and longitudinally furrowed in conjunction with the slightly square shape<br>In later vegetative stages, still generally rounded in appearance with slight furrowing on more recent stem growth<br>Older growth now fuller with lower parts of main stem and oldest branches now with slightly woody appearance and outer texture |
| Stem diameter at base (Unit: cm) | 1.5-4 cm often multiple stems with thinner diameters, depends on nature of initial cutting material |
| Stem color (RHS No.) | Green portions between RHS 144A and 146A at vegetative maturity and during flowering, woody colored tan lower portions of stem are close to 156A-156D |
| Stem pith type | This is highly dependent on the age and/or maturity of the stem<br>Most mature main stem pith is thick to woody |
| Characteristics | Parental variety (1AC) (Female plant) |
| Stem shape | A smooth or slightly longitudinally furrowed texture that can vary throughout the plant.<br>Rigid, straight or flexuous<br>Canescent, scabrous, or rough textured in late growth stage |
| Stem diameter at base (Unit: cm) | 3.0-12 cm in outdoor plants |
| Stem color (RHS No.) | Immature RHS 146D<br>Mature RHS 143C |
| Stem pith type | Moderate to thick |

TABLE IV

| Inflorescence (Female/Pistillate Flowers) | |
|---|---|
| Characteristics | New Variety |
| Flowering (blooming) habit | CW2A produces pistillate flowers in axils at nodal points along main axis and lateral branches for most of the vegetative growth period<br>As flowering begins to develop, these start to become more prolific clusters of individual flowers that appear on increasing branching growth from axillary buds |

TABLE IV-continued

| Inflorescence (Female/Pistillate Flowers) | |
|---|---|
| | emerging from increasingly short internodes on both the main and lateral axes<br>Observations indicated a noted shift to this pattern between 57-73 days after vegetative clones were transplanted outdoors<br>The pointed appearance of the terminal inflorescence buds probably contribute to the overall less dense popcorn appearance of floral clusters along the lateral and main axes<br>Some are quite full and denser more similar to 1 AC, but many are the looser popcorn appearance |
| Proportion of female plants | 100% with some exhibiting monoecious tendencies |
| Inflorescence position | Above<br>Apical portions of main and lateral axes |
| Flower arrangement | Overlapping, Congested, touching, and sometimes stacked |
| Number of flowers per plant | Hundreds to thousands flowers per plant<br>Multitudinous, congested, with high concentrations on bushier wide inflorescence |
| Flower shape | Bilateral symmetry with an overall compressed ovaloid appearance |
| Flower (individual pistillate) length (Unit: mm) | 6-11 mm |
| Flower (compound cyme) diameter (Unit: cm) | 3.0-12.5 cm |
| Corolla | No defined corolla<br>Apetalous pistillate flowers |
| Corolla Color (RHS No.) | N/A |
| Bract shape | Miniature leaf, trichomated, tips of leaflets emergent from dense floral clusters<br>Leaflets number 3 or 5 with many bracts having 5 leaflets<br>The base pair is nearly vestigial<br>Bracts range in length from 2-7 mm or more depending on maturity of flowering spike |
| Bract color (RHS No.) | Adaxial - darkest at tips between RHS 139A to lighter at base of leaflets RHS 147A<br>Abaxial - between RHS 137B and 147B |
| Bracteole shape (general description) | Bracteole is a short, scale-like, Membranous piece of tissue, subtending (and nearly adhering to) the underside of pistillate flowers.<br>It is very similar to the stipules of the plant, but wider, shorter, and buried within the densely clustered pistillate inflorescences and so, not immediately observable without dissection |
| Bracteole color (RHS No.) | Like stipule, vibrant green streak in middle is very close to RHS 141C to thin white papery margins close to RHS 4D, 8D, 11D |
| Calyx shape (general description) | Fused green calyx [bract] (perigonium), membranous, broadly ovate, beaked at the tip, persistent, enclosing the fresh and dry fruit, highly trichomated and take on a frosted appearance |
| Calyx color (RHS No.) | Graduation of color from tip to base: RHS NN137B through 143A-143C, 144B, N144C, 145A-145D, 157A-157D |
| Stigma shape | Short apical style with two long filiform stigmatic branches |

TABLE IV-continued

| Inflorescence (Female/Pistillate Flowers) | |
|---|---|
| | At flower maturity, the pistils senesce to a reddish-brown |
| Stigma length (Unit: mm) | 4-11 mm<br>Generally longer and thinner than '1AC'<br>Pollination, and environmental factors effect state of stigma |
| Stigma color (RHS No.) | Freshly emergent, tips and papillae RHS 1C-1D to 2D and 4C<br>Some have a slight vegetative greenish hue, RHS 144C to 145A<br>When senesced, from a darker RHS 165A to a lighter 164A to 165B |
| Trichome shape | Capitate stalked glandular multiseriate/uniseriate trichomes, especially on flowering inflorescences and perigonial bracts<br>Capitate Sessile glandular trichomes on stems, leaves, and bracts |
| Cystolithic non-glandular | Cystolithic non-glandular trichomes on leaves |
| Trichome color (RHS No.) | RHS 4D and 155A and NN155A-NN155D, creamy color of varying saturation |
| Terminal bud shape | Terminal buds are naked, vegetative, and mixed depending on life stage (vegetative/flowering) |
| Terminal bud color (RHS No.) | Many emergent pistillate flowers, RHS NN137B through 143A-143C, 144B, N144C, 145A-145D, 157A-157D,<br>Emergent bract leaflets RHS 147A<br>Freshly emergent stigmas, tips and papillae RHS 1C-1D to 2D and 4C<br>Some have a slight vegetative greenish hue, RHS 144C to 145A |
| Pedicel | Absent (sessile) |
| Staminate shape | Minute or reduced to absent (sessile) in pistillate flowers<br>Present in staminate flowers |
| Sepal color (RHS No.) | RHS 10D at end near papery edges with vegetative streaks down center of each sepal, N144B to N144C, depending on maturity |
| Pollen description | N/A |
| Seed description | Light to Dark brown, mostly dark brown with speckling<br>Seeds (achenes) are encased in trichomated leaf-like fused bract (perigonium), solitary, ovoid, and slightly compressed<br>Pericarp is dry and brittle, finely reticulate; endosperm is fleshy; embryois curved; cotyledon is fleshy<br>Seeds (achenes) are solitary, ovoid, 4-7 mm in length<br>Typically, seeds weigh 0.01 g-0.02 g each<br>Variation in seed size and color are observed due to environmental conditions |
| Marbling of seed | Medium |
| Petal description | Apetalous (petals absent in flowers, but sepals present on staminate flowers) |

| Characteristics | Parental variety (1AC) (Female plant) |
|---|---|
| Flowering (blooming) habit | Early flower primordia appear at the base of petioles, with a pair of white stigmas emerging from each perigonal bract.<br>Pistillate compound inflorescences are congested pseudospikes with leaf-like bracts, leafy and compact, with the largest inflorescences present on dominant apical stems |

TABLE IV-continued

| Inflorescence (Female/Pistillate Flowers) | |
|---|---|
| | Female flowers are small but numerous and take on the coloration present in the vegetation of the specimen (typically green); enclosed and surrounded by a fused calyx (perigonal bract), entire, beaked at the tip; unilocular ovary superior, sessile, with two long filiform stigmatic branches which are white upon emergence and later deteriorating to reddish-brown<br>Flowers may form on the entire length of the stem; however, inflorescences are most conspicuous at the top of the plant.<br>Flowers and inflorescences are covered with glandular trichomes |
| Proportion of female plants | 100% |
| Inflorescence position | Above<br>Apical portions of main and lateral axes |
| Flower arrangement | Overlapping, Congested, touching, and sometimes stacked |
| Number of flowers per plant | Hundreds to thousands flowers per plant<br>Multitudinous, congested, with high concentrations on bushier wide inflorescence |
| Flower shape | Bilateral symmetry with an overall compressed ovaloid appearance |
| Flower (individual pistillate) length (Unit: mm) | 8-14 mm |
| Flower (compound cyme) diameter (Unit: cm) | 7 cm-15 cm |
| Corolla | No defined corolla<br>Apetalous pistillate flowers |
| Corolla Color (RHS No.) | N/A |
| Bract shape | Miniature leaf, trichomated, tips of leaflets emergent from dense floral clusters<br>Leaflets number 3, 5, or 7 with many bracts having 5 leaflets |
| Bract color (RHS No.) | Adaxial - darker tips are RHS NN137A to a brighter (yellower) green N144C-D at the base of leaflets and in the venation<br>Abaxial - RHS 147B-147C leaf and 148B-148C venation<br>Some plants feature bracts with Increasing purplish coloration that is blended with the dark green color for an overall appearance very similar to RHS N92A |
| Bracteole shape (general description) | Bracteole is a short, scale-like, Membranous piece of tissue, subtending (and nearly adhering to) the underside of pistillate flowers<br>It is very similar to the stipules of the plant, but wider, shorter, and buried within the densely clustered pistillate inflorescences and so, not immediately observable without dissection |
| Bracteole color (RHS No.) | Vibrant Green center of bracteole is RHS 143A-143B, the papery white edge is similar to NN155B-NN155C |
| Calyx shape (general description) | Fused green calyx [bract] (perigonium), membranous, broadly ovate, beaked at the tip, persistent, enclosing the fresh and dry fruit, highly trichomated and take on a frosted appearance |
| Calyx color (RHS No.) | Some RHS 137A-137D, some 141A-141C, to 143C or 144A-144D or 145A, to 150D or 155A-155B at lighter base |

TABLE IV-continued

| Inflorescence (Female/Pistillate Flowers) | |
|---|---|
| Stigma shape | Short apical style with two long filiform stigmatic branches<br>At flower maturity, the pistils senesce to a reddish-brown |
| Stigma length (Unit: mm) | 6-9 mm<br>Pollination, and environmental factors effect state of stigma |
| Stigma color (RHS No.) | RHS 150A-150C or 151C-151D when freshly emergent to 8B when around maturity or past maturity, to 164A or 166A-166D or 174A-174B or 175D when senescent |
| Trichome shape | Capitate stalked glandular multiseriate/unisefiate trichomes, especially on flowering inflorescences and perigonial bracts<br>Capitate Sessile glandular trichomes on stems, leaves, and bracts<br>Cystolithic non-glandular trichomes on leaves |
| Trichome color (RHS No.) | Variable<br>Clear, white; :translucent at first, as it matures, cloudy to amber as phytochemicals enter the trichome glandular head |
| Terminal bud shape | Terminal buds are naked, vegetative, and mixed depending on life stage (vegetative/flowering) |
| Terminal bud color (RHS No.) | Multicolored |
| Pedicel | Absent (sessile) |
| Staminate shape | Absent |
| Sepal color (RHS No.) | N/A |
| Pollen description | N/A |
| Seed description | Seed coat with solid pale grey or grey/brown/white to light - dark brown coloration when mature<br>Seeds (achenes) are solitary, ovoid, 3-6 mm in length<br>Seed weight is typically varied with masses within the range of 0.006 g-0.016 g |
| Marbling of seed | N/A |
| Petal description | Apetalous (petals absent in flowers) |

TABLE V

| Other Characteristics | |
|---|---|
| Characteristics | New Variety |
| Time period and condition of flowering/ blooming | Female flower initiation occurs in plants when the daylight photoperiod has 14 hours of daylight hours within a 24-hour period, with 10 hours of continuous darkness during the nocturnal duration<br>Timing of flowering is largely dependent (if not entirely) on photoperiod |
| Proportion of hermaphrodite plants | Lower (~10%) in vegetative clones<br>More moderate in populations from seeds harvested from fields (segregating population and not necessarily selfed) |
| Hardiness of plant | Resistant to frost (without freezing rain) in early and late growth stages<br>Resistant to cold in late vegetative and mature stages<br>Hardy to tolerate of moist and damp conditions without showing stress<br>Not tolerant to soil oversaturated with water for long periods |

TABLE V-continued

| Other Characteristics | |
|---|---|
| | Hardy to tolerate of moist and damp conditions without |
| Breaking action | Branches are highly flexible.<br>Typically, plants lean over more than 1AC check variety<br>Plants are resistant to complete lodging<br>Central stem is strong. Stem breakage usually does not occur |
| Seed shattering | About 30-50% of seeds shatter readily if plants are grown in field |
| Rooting rate after cutting/cloning | 95-99%<br>Adventitious roots typically form day 5-day 14<br>Roots fill a two-inch pot completely in Day 21-35 |
| Total THC and CBD content at harvest maturity | Total CBD content: 4.50-6.24%<br>Total THC content:Total CBD 0.13-0.27%<br>Total CBD:Total THC (ratio) = 23:1 |

| Characteristics | Parental variety (1AC) (Female plant) |
|---|---|
| Time period and condition of flowering/ blooming | Specifically, a photoperiod of no less than 11 hours of continuous darkness within a 24-hour period.<br>Often flowers three to four weeks after 'CW2A' |
| Proportion of hermaphrodite plants | N/A |
| Hardiness of plant | Resistant to frost (with nightly temperatures as low as 27 degrees Fahrenheit as long as the temperature rises during the day to melt and dry previous frost found on leaves)<br>Resistant to cold in late vegetative growth stages<br>Cold resistance increases during the late flowering stage<br>When subjected to cold temperatures (such as less than 45 degrees Fahrenheit) for longer than 6 hours a day, plants show signs of cold shock and growth rates are reduced showing signs of stress if adequate drainage allows damp conditions to be a temporary occurrence<br>More drought tolerant in clay loam and heavier soils, while less drought tolerant in sandy loam and lighter soils<br>Over watering is noticeable during the early stages of vegetative growth when plant root structures are more sensitive, or if no adequate drainage exists |
| Breaking action | Branches are less flexible<br>Typically, plants do not lean and are very sturdy<br>Plants can tolerate high winds easily without lodging<br>Stem branches can break or split in hail storms, however this is rare |
| Seed shattering | Seeds do not shatter readily, but are mostly persistent |
| Rooting rate after cutting/cloning | 92-98%<br>Adventitious roots typically form day 10-day 21<br>Roots fill a two-inch pot completely in Day 28-45 |

TABLE V-continued

| Other Characteristics | |
|---|---|
| Total THC and CBD content at harvest maturity | content: 5-8%<br>Total THC content: 0.2-0.3%<br>Total CBD:Total THC (ratio) = 26:1 |

Figure 10:
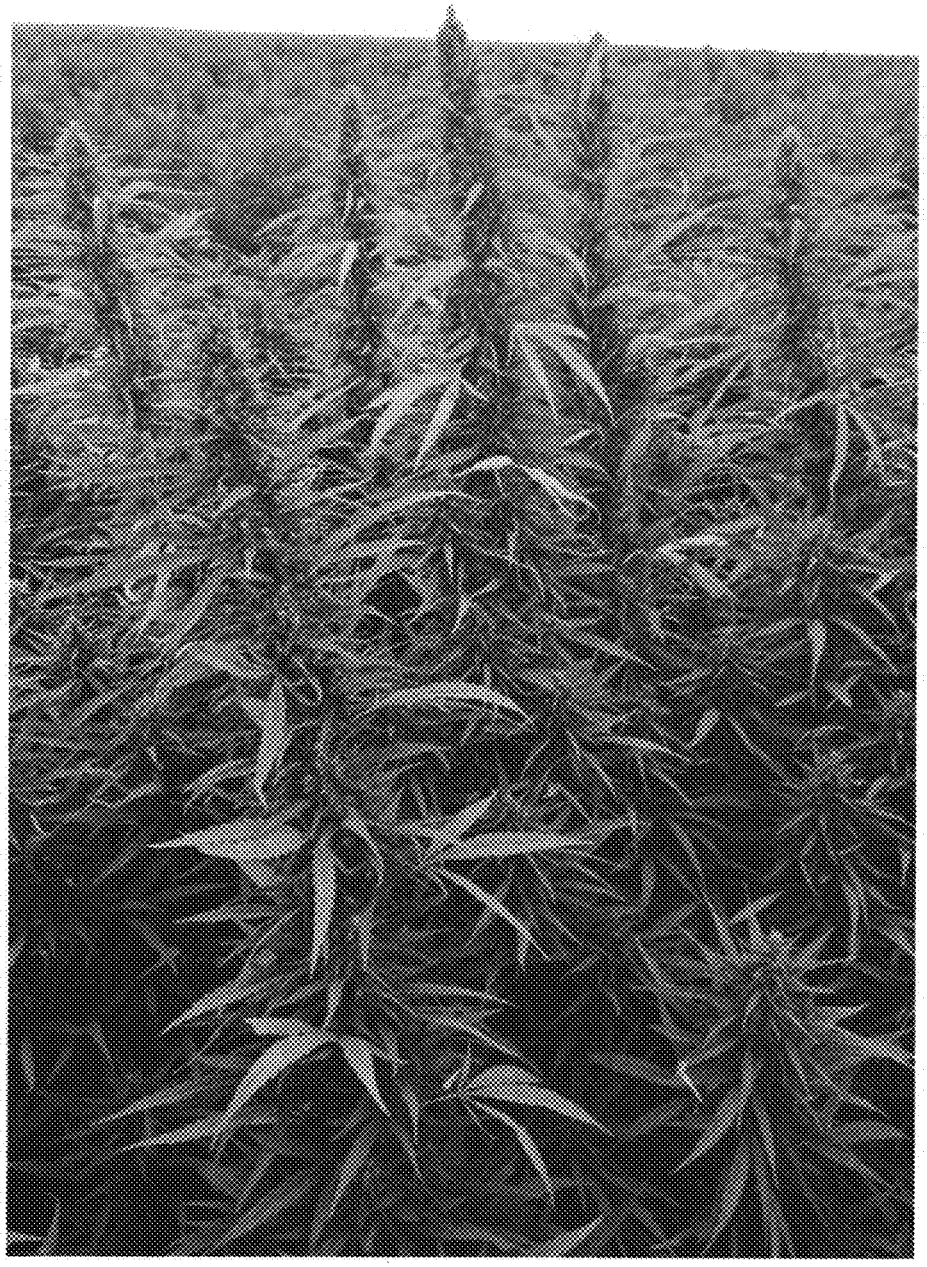
FIG. 10 shows an overall view of the 'CW2A' outdoor plant at the harvest maturity as grown in the field.
Figure 11:
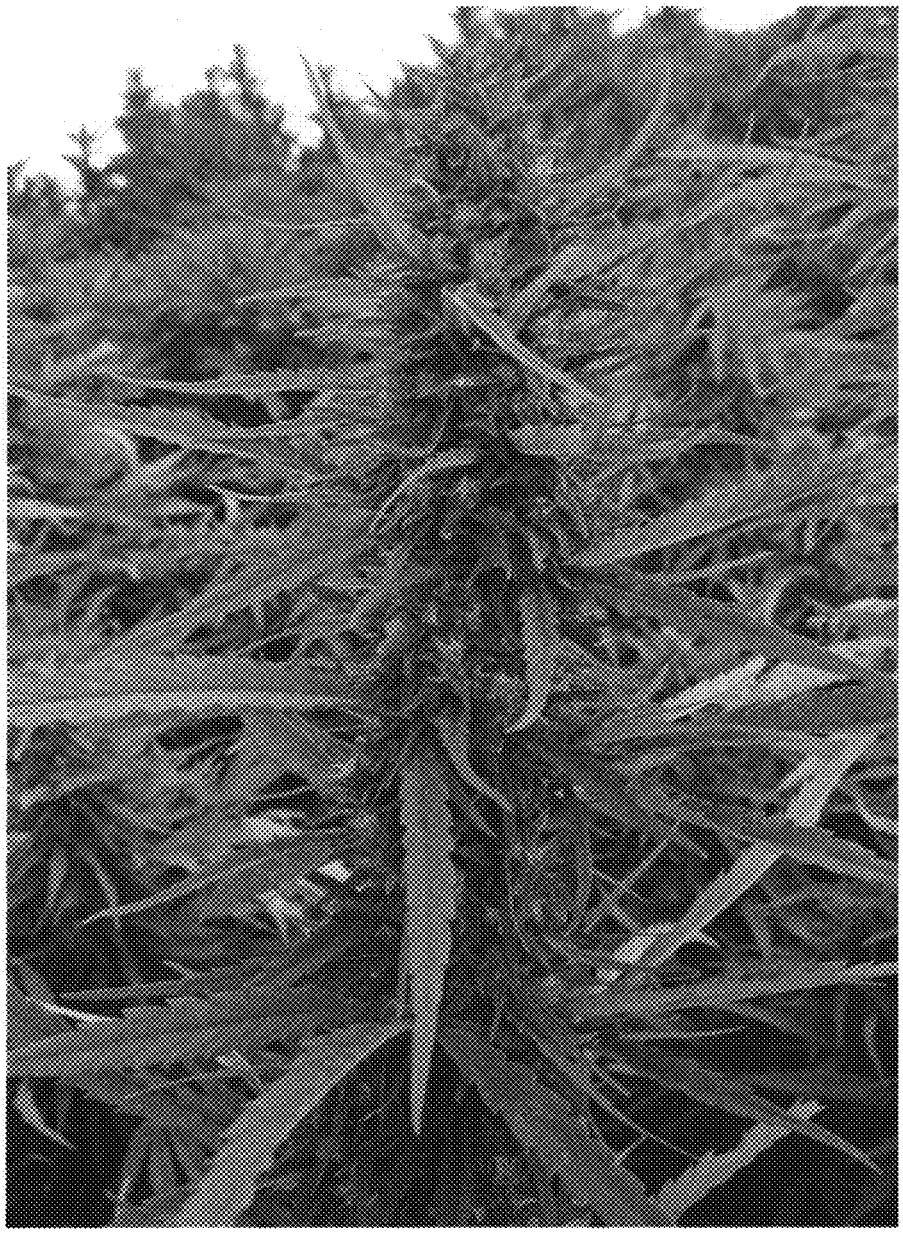
FIG. 11 shows an overall view of upper part (including flowers) of the 'CW2A' outdoor plant at the harvest maturity as grown in the field.
Figure 12:
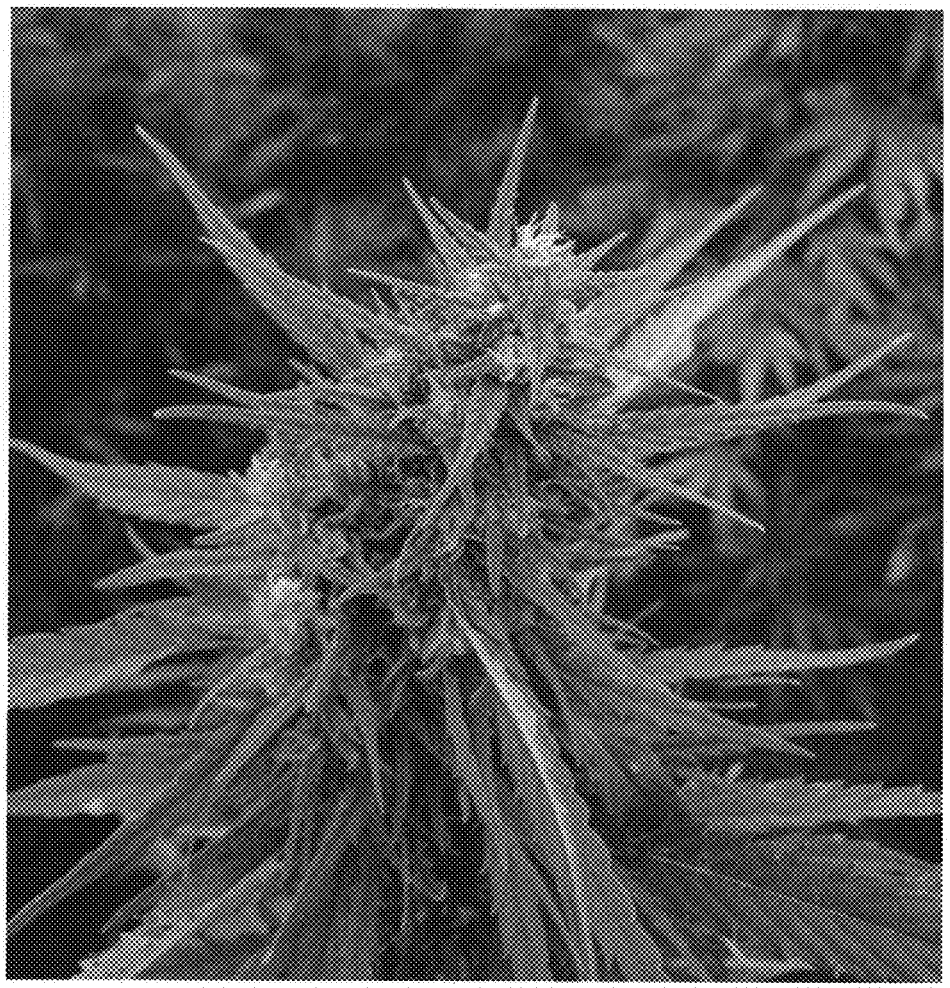
FIG. 12 shows a close view of flowers of the 'CW2A' outdoor plant at the harvest maturity as grown in the field.
Figure 13:
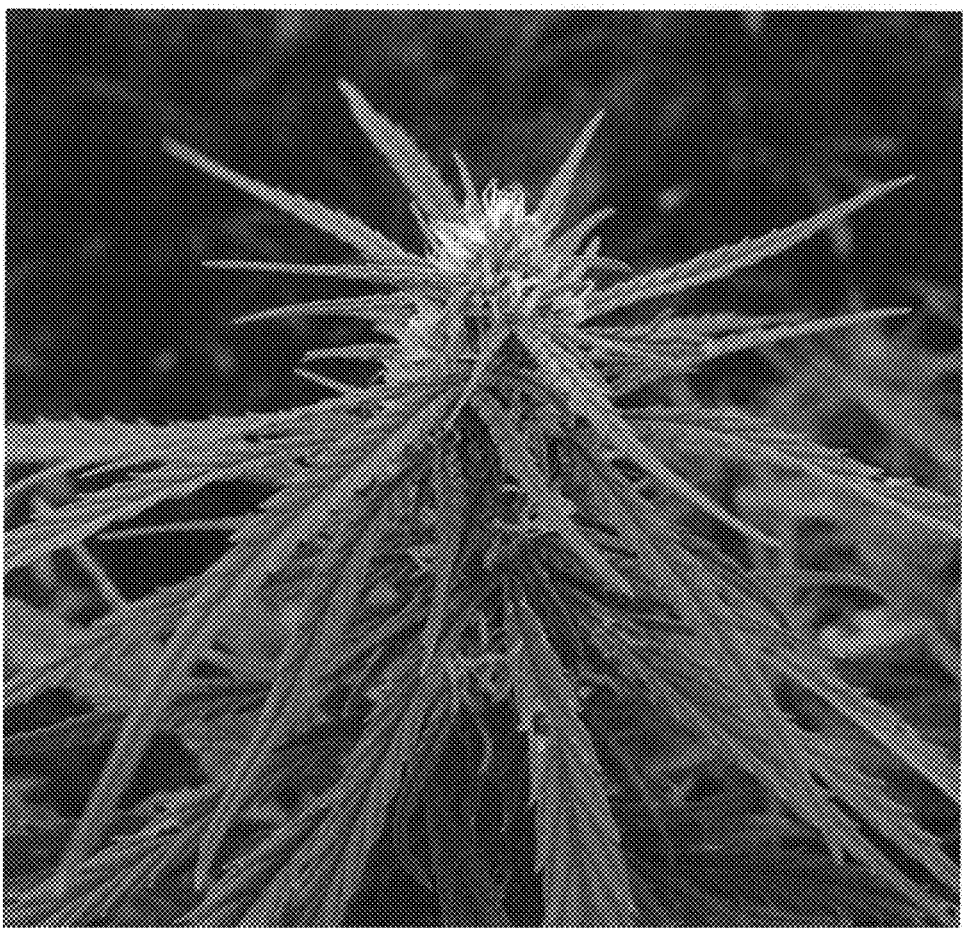
FIG. 13 shows another close view of flowers of the 'CW2A' outdoor plant at the harvest maturity as grown in the field.

As used herein, the term "maturity", "harvest maturity," or "floral maturity" refers to the developmental stage at which the 'CW2A' plant is harvested. Persons having skill in the art will recognize maturity based on the plant's morphologies. It is also good practice to conduct periodic cannabinoid content (i.e., potency) tests throughout the development of the plant to ensure that harvest occurs at maturity. The 'CW2A' plant is considered to be at harvest maturity when fan leaves begin to yellow, and when inflorescences begin to take on a 'frosted' appearance, as trichomes develop on calyxes and lower portions of bracts. If bracts and inflorescent parts turn overly yellow and/or if the 'frosted' appearance is visible from afar, this could indicate the plant is beyond maturity. The color of trichomes can also be used to determine maturity. Trichomes from the 'CW2A' plant first look small and clear, but gradually enlarge, and progressively become 'milkier' and opaque with continued maturation, finally displaying a desiccated appearance and amber color. In the present disclosure, harvest maturity is defined as the time period between the enlarged clear trichome developmental stage and the opaque/milky trichome developmental stage. Amber trichomes in the 'CW2A' plant are an indication of overly mature trichomes. In some embodiments, the harvest maturity of the 'CW2A' variety is typically around 15 and ½ weeks after planting vegetative cuttings in the field. Growing conditions throughout the plant's life cycle, nutrient variations, and environmental factors can all influence the amount of time for 'CW2A' plants to reach harvest maturity. The present disclosure uses the terms "maturity," "harvest maturity," and "floral maturity" interchangeably. FIGS. 10-13 provide photographs of the 'CW2A' plant at harvest maturity.

In some instances, the botanical descriptions disclosed herein reflect the range of phenotypical variation observed under indoor and outdoor growth conditions. Total Potential THC/CBD contents presented in this document reflect the total potential (i.e., decarboxylated) THC and CBD content after decarboxylation of the THCA and CBDA contents of the sample. The formula used for this calculation is reproduced below for the Office's convenience. Total THC=THC+(THCA*(0.877)). Total CBD=CBD+(CBDA*(0.877)).

When 'CW2A' is compared to the feral male parent (a.k.a. ditch weed), 'CW2A' is taller in plant height, but narrower in plant width than the feral male parent. The *indica*-dominant feral male parent having a squat statute are shorter than 'CW2A' and branch wider with wider leaves than 'CW2A'.

When 'CW2A' is compared to the proprietary female parent ('1AC'), 'CW2A' is taller in plant height, but narrower in plant width than '1AC'. Generally, 'CW2A' is twice as tall as it is wide, while '1AC' has a similar ratio of plant height to width. 'CW2A' with 19-29 teeth of middle leaflet has narrower leaflets than '1AC' with 26-37 teeth of middle leaflet. Regarding petiole length at maturity, 'CW2A' is in general shorter than '1AC'. Regarding stem diameter at base, 'CW2A' is in general shorter than '1AC'. When comparing individual flower length and compound cyme diameter, 'CW2A' is smaller in size than '1AC'. On the other hand, 'CW2A' has generally a longer and thinner stigma than '1AC'. While '1AC' does not show hermaphroditic tendency, hermaphroditic plants are observed from 'CW2A' depending on growth conditions. Since 'CW2A' branches are highly flexible, 'CW2A' plants lean over more than '1AC' that has less flexible branches. With regard to time to harvest seeds, 'CW2A' shows a shorter harvest time than '1AC'. After stem cutting from vegetative and/or flowering plants, adventitious roots of 'CW2A' emerge and grow faster than '1AC'.

When 'CW2A' is compared to the known *Cannabis* plant named 'ECUADORIAN *SATIVA*' (U.S. Plant Pat. No. 27,475), there are several distinctive characteristics. For example, 'CW2A' plant is generally taller than the 'ECUADORIAN *SATIVA*' plant. While the aroma of 'ECUADORIAN *SATIVA*' is strongly mephitic with hints of limonene, 'CW2A' has an earthy aromatic herbal smell with a hint of citrus and/or pine scent and a general sweetness. 'CW2A' stem diameter at base is greater than 'ECUADORIAN *SATIVA*'. Also, individual pistillate flowers and stigma of 'CW2A' are longer than those of 'ECUADORIAN *SATIVA*'. Furthermore, there is a significant difference in total THC content between 'CW2A' and 'ECUADORIAN *SATIVA*'. The total THC content of 'CW2A' is between 0.13-0.27%, rendering the claimed plant a hemp plant under U.S. law. 'ECUADORIAN *SATIVA*' on the other hand, accumulates 12.45% total THC, resulting in a different classification of the plant.

The following is a detailed description of the new cultivar of 'CW2A'. The following description is for plants that are vegetative and reproductive stages from seedling to 12 weeks old as of the time of the measurements.

General description:

*Plant life form and habit.*—An herbaceous, upright, dioecious annual plant with hermaphroditic tendencies depending on growth conditions.

Classification:

*Denomination.*—'CW2A'.

*Species.*—*Cannabis sativa* L.

Origin, form, and growth characteristics:

*Origin.*—Progeny plant derived from a controlled-cross between proprietary cultivar '1AC' as the female parent (i.e., pollen accepter) and Feral Male Parent (i.e., pollen donor), as described in detail above.

*Propagation.*—The strain is asexually propagated by vegetative stem cuttings as well as stem cuttings from flowering plants.

*Propagation ease.*—Easy.

*Propagation condition.*—Adventitious root structures readily form from stem tissue when submerged in rooting media, including soil, rockwool, aeroponics, etc., when adequate amounts of oxygen and moisture are supplied, and ambient temperatures are between 55-75° F. with appropriate lighting conditions.

Plant:

*Height.*—1-4 m at maturity.

*Width.*—0.4-2 m.

*Vigor.*—High (very vigorous).

*Time to harvest.*—100-135 days.

*Pest susceptibility.*—Resistant to common viruses and fungal disease.

*Genetically modified organism.*—No.

Leaf/foliage:

*Arrangement*.—Opposite in early vegetative growth stages especially on main axis if grown from seed; A tendency toward alternate arrangements on axillary branches once the flowering stage begins or when taken as a vegetative cutting typically observed.

*Shape*.—Palmately compound.

*Structure*.—Serrated margins, lightly acicular to lanceolate leaflets, tapering to an acuminate apex.

*Margin*.—Jaggedly serrate with each tooth apex angled toward leaflet apex; apical side of tooth is concave and basal side of tooth is convex.

*Hair*.—Absent.

*Leaf (with petiole) length at maturity*.—12-24 cm.

*Number of leaflets*.—3-5 in immature plants, as many as 9 at maturity.

*Middle largest leaflet length*.—7-15.9 cm.

*Middle largest leaflet width*.—1.5-2.0 cm.

*Middle largest leaflet length/width ration*.—About 4:1-8:1.

*Number of teeth of middle leaflet (average)*.—19-29.

*Color*.—Upper side (Adaxial) — 137A (vegetative growth stage before flowering); very close to NN137A (during flowering stage).

*Color*.—Lower side (Abaxial) — Between 146D and 147C (vegetative growth stage before flowering); between NN137D and 147B (during flowering stage).

*Leaf glossiness*.—Very slight sheen, but not glossy.

*Veins/midrib shape*.—Midvein is straight down the middle of each leaflet; Secondary veins are percurrent, branched alternately from midvein, and grow to tooth apex.

*Vein/midrib color*.—143C.

Petiole:

*Petiole length*.—4.2-8.0 cm.

*Petiole color*.—Very slightly lighter than 144A.

*Anthocyanin color in petioles*.—59A to 187A and 187B when present.

*Anthocyanin intensity in petioles*.—(i) Total absence to minute but pronounced mixture with normal green coloration on adaxial surface of petiole during vegetative growth stage; (ii) anthocyanin pigmentation on petioles intensifies and covers both adaxial and abaxial surfaces during flowering stage; darker adaxial surfaces are still 59A to 187A; Abaxial surfaces are lighter and less densely colored with a range of coloration 184A; to 180A; to 178A through 178B; to 176A.

*Stipule shape*.—Up to 1.0 cm, spinose with a wider base about 1.0 mm or more thick tapering to spinose tip; light green center with white green edges and a folded, v-shape in cross section; sometimes curvaceous growth.

*Stipule length*.—0.4-0.9 cm.

*Stipule color*.—Green portions of stipule vary from 143A to the light yellow white of the edges 4D.

Stem:

*Shape*.—Round at maturity; very slightly squared in immature axillary branches and at immature growth stages; finely pubescent and longitudinally furrowed in conjunction with the slightly square shape; in later vegetative stages, still generally rounded in appearance with slight furrowing on more recent stem growth; older growth fuller with lower parts of main stem and oldest branches with slightly woody appearance and outer texture.

*Diameter*.—1.5-4 cm often multiple stems with thinner diameters, depends on nature of initial cutting material.

*Color*.—Green portions between RHS 144A and 146A at vegetative maturity and during flowering, woody colored tan lower portions of stem are close to 156A-156D.

*Pith type*.—Thick to woody for a mature main stem pith; but this is highly dependent on the age and/or maturity of the stem.

Inflorescence:

*Blooming/flowering habit*.—CW2A produces pistillate flowers in axils at nodal points along main axis and lateral branches for most of the vegetative growth period; as flowering begins to develop, these start to become more prolific clusters of individual flowers that appear on increasing branching growth from axillary buds emerging from increasingly short internodes on both the main and lateral axes; observations indicated a noted shift to this pattern between 57-73 days after vegetative clones were transplanted outdoors; the pointed appearance of the terminal inflorescence buds probably contribute to the overall less dense popcorn appearance of floral clusters along the lateral and main axes; some are quite full and denser more similar to 1AC, but many are the looser popcorn appearance.

*Inflorescence position relative to foliage*.—Above.

*Flower arrangement*.—Overlapping, Congested, touching, and sometimes stacked.

*Number of flowers per plant*.—Hundreds to thousands of flowering sites.

Flowers:

*Shape*.—Bilateral symmetry with an overall compressed ovaloid appearance.

*Flower (individual pistillate) length*.—6-11 mm.

*Flower (compound cyme) diameter*.—3.0-12.5 cm.

*Corolla shape*.—No defined corolla.

*Corolla color*.—N/A.

*Bract shape*.—Miniature leaf, trichomated, tips of leaflets emergent from dense floral clusters; leaflets number 3 or 5 with many bracts having 5 leaflets; the base pair is nearly vestigial.

*Bract size*.—2-7 mm or more depending on maturity of flowering spike.

*Bract color*.—Adaxial — darkest at tips between 139A to lighter at base of leaflets 147A; Abaxial — between 137B and 147B.

*Bracteole color*.—Vibrant green streak in middle is very close to 141C to thin white papery margins close to 4D, 8D, and 11D.

*Stigma shape*.—Short apical style with two long filiform stigmatic branches.

*Stigma length*.—4-11 mm.

*Stigma color*.—Freshly emergent, tips and papillae 1C-1D to 2D and 4C; some have a slight vegetative greenish hue, 144C to 145A; When senesced, from a darker 165A to a lighter 164A to 165B.

*Trichome shape*.—Capitate-stalked glandular multiseriate/uniseriate trichomes, especially on flowering inflorescences and perigonial bracts.

*Trichome color*.—4D, 155A and NN155A-155D.

*Cola (terminal bud) shape*.—Naked, vegetative, and mixed depending on life stage (vegetative/flowering).

*Cola (terminal bud) color*.—Many emergent pistillate flowers, NN137B through 143A-143C, 144B, N144C, 145A-145D, 157A-157D; emergent bract leaflets 147A; freshly emergent stigmas, tips and papillae 1C-1D to 2D and 4C; some have a slight vegetative greenish hue, 144C to 145A.

*Pedicel*.—Absent.

*Pedicel color*.—N/A.

*Staminate flower*.—Minute or reduced to absent (sessile) in pistillate flowers.

*Sepal color*.—10D at end near papery edges with vegetative streaks down center of each sepal, N144B to N144C, depending on maturity.

*Pollen*.—N/A.

*Seed*.—Textured, globular, and encased in trichomated leaf-like fused bract (perigonium), solitary, ovoid, and slightly compressed. Seeds weigh 0.01 g-0.02 g each.

*Seed length*.—Typically 4-7 mm in length.

*Marbeling of seed*.—Medium.

*Petal*.—Apetalous (petals absent in flowers, but sepals present on staminate flowers).

Other characteristics:

*Aroma*.—Earthy aromatic herbal smell with a hint of citrus/pine scent and a general sweetness.

*Proportion of hermaphrodite plants*.—Lower (~10%) in vegetative clones; more moderate in populations from seeds harvested from fields (segregating population and not necessarily selfed).

*Hardiness*.—Hardy to tolerate moist and damp conditions without showing stress.

*Breaking action*.—Branches are highly flexible. Central stem is strong so that stem breakage usually does not occur.

*Seed shattering*.—About 30-50% of seeds shatter readily if plants are grown in the field.

*Rooting rate after cutting/cloning*.—CW2A rooting rate is 95-99% on average; vigorous.

*Total THC and CBD content at harvest maturity*.—(i) Total THC content: 0.13% to 0.27%; (ii) Total CBD content: 4.50% to 6.24%.

In addition, provided herein are further descriptions of the new cultivar of 'CW2A' CW2A has the following characteristics:

Growth Habit:

CW2A plant has long and slender leaflets/leaves and is 1-4 meters in height at maturity depending on growth conditions ("*sativa*-dominant"). Monoecious characteristics without stress manipulation are not common, but occasionally observed. Dioecious plant has hermaphroditic tendencies.

CW2A also shows premature flowering without change in light duration though it is still responsive to light/dark cycle (12/12 hours) for inducing flowering. Elongated nodes bear palmately compound leaf structures on elongated petioles. Nodes tend to stack in early growth stages and elongate in later parts of vegetative growth. In immature vegetative growth stages, the plant often shows flower primordia or fully formed flower structures as evidenced by pairs of white, hair-like stigmatic tendrils at nodal branch points. Inflorescences are long and spear like indeterminate inflorescences.

Flowering and Seed Formation:

Timing of flowering is largely dependent (if not entirely) on photoperiod.

Week 1-Week 2 vigorous growth, pistillate flowers are already present, the maturity rate and pistillate flowers grow very rapidly and multiply, pistillate flowers are in prime condition for pollination and beginning seed formation in early flowering stages due to monecious characteristics.

Week 2-Week 4 vigorous growth continues, more pistillate flowers grow and begin forming first bud like structure between two and three weeks, pistillate flowers are in prime condition for seed formation up to three and a half weeks.

Week 4-Week 6 vigorous growth slows down, buds begin to swell, plant has nearly doubled in size from last day of vegetative stage, bud characteristics begin to mature, plant terpenes are at their peak potency at 6 weeks, male staminate flowers begin to form and open (yellow banana shaped sacs).

Week 6-Week 8 buds begin to swell to full potential, seeds begin to form and mature at internodes and within flower buds, all characteristics are realized, yellowing of the leaves occur naturally, cannabidiol compounds are at their peak at week 8, leaves begin to naturally yellow.

Week 8-Week 10 leaves dry, leaves and seeds drop, volatile terpene compounds extremely diminish, cannabidiol compounds slowly diminish.

Growth Conditions:

Vegetative Stage 75-85 degrees F. is ideal, temps up to 90 degrees F. are not harmful, 40-60% relative humidity.

Flowering Stage 75-85 degrees F. (nights getting cooler, as low as 40 degrees F.), 40-50% relative humidity.

In another embodiment, temperature and humidity ranges may be decreased or increased to account for all weather conditions.

Shape of Plant at Maturity:

long and spear like flowers, bushy but elongated branches, height and shape depends on planting pattern, when planted with space (5 feet apart), plant bushes and is 5-6 feet tall, when planted close (2 feet or less apart), plant is longer and more string/spear flower characteristics and be up to 12 feet tall.

Branching Habits:

dependent upon planting pattern. With sufficient space, the plant forms branches 360 degrees with a concentration of branches forming toward the sun or light source. The branches are long, spear like, and have tendency to break in high winds due to its length (flower and leaf surface area). Node length on branches start very short in early vegetative stage and elongate as the plant matures. Full flower internode length can be up to 3" inches long.

Rooting Ability:

Roots grow easily under the proper environment starting from propagation that comprises a temperature of about 70-75 degrees Fahrenheit, 50% relative humidity, 35-55% moisture content in the soil or media, and appropriate lighting.

Feeder roots grow 360 degrees, are typically found 3" inches below ground level, and stay in the top 18" inches of soil. Brace roots typically stay within the center of the plant and can go as deep as 3 feet for maximum stability in windy conditions.

Timing of Duration of Flowering Session:

The timing of the flowering duration is dependent on the degrees latitude positioned on the globe. The dates are dependent on the northern or southern hemisphere. Northern Hemisphere is used below:

40-50 degrees latitude typically begins flowering stage July 5-July 15 to full maturity September 10-September 20; 30-40 degrees latitude typically begins flowering stage July 15- July 25 to full maturity September 20-September 30; 15-30 degrees latitude a later and longer flowering duration is assumed; 0-15 degrees latitude flowering will occur any time of the year because of consistent 12-13 hours of sunlight/day.

In another embodiment, temperature and time ranges may be decreased or increased to account for location change.

Botanical Description of CW2A:

Bark:

tan colored with inner bast fibers running vertical between the inner woody core and bark.

Buds:

1"-5" inches thick, long and resembling spears, spiral pattern early but much more full bud like structures later on, medium on density scale.

Blossoms:

occur predominantly in males but are present in nearly all females, yellow oval sac shapes, Male sacs open in early flowering stages of week 2 through week 4, Females will open later from week 4 through week 6.

Leaves are developed in early vegetative stage, leaves are jagged, long and skinny, large leaves, larger leaves if started from seed.

Fruit:

described in the buds, full essence and character is not recognized until week 6 in flower.

Fragrance:

earthy and light smoky with a hint of piney mint.

Disease Resistance:

resistant to common viruses and fungal diseases,

In the wrong soil conditions, fungal diseases can occur, susceptible to molds and mildews if grown indoors without proper ventilation and high relative humidity (constantly greater than 60% relative humidity).

Drought Resistance:

more tolerant in clay loams and higher organic content soils.

less tolerant in sandy loams with lower organic content soils.

Cold Resistance:

not resistant to cold though germination and emergence. If the plant is exposed to less than 45 degrees Fahrenheit for longer than 6 hours, shock and much lower germ rate will occur.

more resistant to cold in later vegetative and mature state. The plant can withstand between 40 and 45 degrees Fahrenheit for long durations but will show signs of stress and cold shock.

very resistant to cold only late in flowering stage with greater root structures. The plant can withstand several days of frost and temperatures as low as 29 degrees Fahrenheit for less than 5 hours. In this condition, the plant will show extreme shock but will not die.

Damp Resistance:

Plant can take moist and damp conditions without showing stress if in outside conditions and planted in the ground.

Plant does not like to be in oversaturated soil for long periods. Stress will occur showing an intense shrinking and curling of the leaves and nodes.

Productivity (Sunlight, Soil, Water):

Sunlight:

too much direct sunlight does not affect the plant in a harmful way.

does need a minimum of 6 hours of direct sunlight for healthy and fruitful flowering cycle.

Soil:

most productive in sandy loams where water can drain easily. This is only most productive with proper irrigation.

pH of 6.8-7.4 is ideal for outdoor farming.

pH of 6.4-6.7 is ideal for indoor and pH of 5.5-5.8 for hydroponic systems.

Water:

Levels of trace minerals are effective and calcium levels of 200-400 ppm. PH of at or close to 7 is ideal for outdoor farming. PH 6.4-6.7 is best indoors and lower for hydroponics.

Precocity (Flowering, Fruiting, or Ripening Early):

Volatile compounds and plant terpenes are at their peak 2-3 weeks before plant maturity.

Cannabidiol compounds peak 2-3 weeks before seed maturity.

Vigor:

Plant shows vigorous growth in late vegetative stage and the most in the first 2 weeks of flowering stage.

Coloration:

deep forest green at optimal health,

Plant shows different discoloration patterns at signs of nutrient deficiency, yellowing in late flowering stage is natural.

Market Use:

medical drugs foods (e.g. salad oil, margarine, food supplements, etc.)

drinks (e.g. infused beverages, sport drinks, etc.)

technical products (e.g. oil pants, varnishes, fuel, print inks, solvents, coatings etc.)

personal hygiene products (e.g. cosmetics, soap, shampoo, bath gels, etc.)

hemp-infused pet treats textile (e.g. apparel, diapers, fabrics, denim, socks, shoes, fine textiles, twine, rope, carpets, geotextiles, etc.)

building materials (e.g. fiberboard, insulation material, cement blocks, etc.)

The invention claimed is:

1. A new and distinct cultivar of hemp plant named 'CW2A' substantially as shown and described herein.

* * * * *